United States Patent

Burchell

[11] Patent Number: 5,143,224
[45] Date of Patent: Sep. 1, 1992

[54] METHOD AND APPARATUS FOR SEPARATING DIAMONDS FROM ASSOCIATED GANGUE

[75] Inventor: Steven P. Burchell, Farnham, United Kingdom

[73] Assignee: Turret Holdings Limited, British Virgin Isls.

[21] Appl. No.: 667,430

[22] Filed: Mar. 11, 1991

Related U.S. Application Data

[63] Continuation-in-part of Ser. No. 488,378, Feb. 23, 1990, abandoned, which is a continuation of Ser. No. 188,799, filed as PCT/GB87/00565, Aug. 11, 1987, abandoned.

[30] Foreign Application Priority Data

Aug. 20, 1986 [GB] United Kingdom ............... 8620247

[51] Int. Cl.⁵ ............................................. B07C 5/342
[52] U.S. Cl. .................................. 209/579; 209/906; 356/30; 356/301
[58] Field of Search ............... 209/576, 577, 579, 587, 209/589, 906; 356/30, 301, 317, 318, 441

[56] References Cited

U.S. PATENT DOCUMENTS

| | | | |
|---|---|---|---|
| 3,906,241 | 9/1975 | Thompson | 250/227.23 X |
| 4,212,397 | 7/1980 | Bockelmann | 209/589 |
| 4,323,159 | 4/1982 | Wolf | 209/576 X |
| 4,397,556 | 8/1983 | Muller | 356/301 |
| 4,693,377 | 9/1987 | Gerrard et al. | 209/579 |
| 4,799,786 | 1/1989 | Gerrard | 356/301 X |
| 4,907,875 | 3/1990 | Bowley et al. | 356/30 |
| 4,919,533 | 4/1990 | Bowley et al. | 356/30 |

FOREIGN PATENT DOCUMENTS

| | | | |
|---|---|---|---|
| 0071462 | 2/1983 | European Pat. Off. | |
| 0341096 | 11/1989 | European Pat. Off. | 209/579 |
| 2429624 | 2/1980 | France | 209/579 |
| 2073410 | 10/1981 | United Kingdom | 209/589 |
| 2233759 | 1/1991 | United Kingdom | 209/589 |

OTHER PUBLICATIONS

Santavicca, Domenic, "A High Energy, Long Pulse Nd:YAG Laser Multipass Cell for Raman Scattering Diagnostics", *Optics Communications*, Sep. 1979, pp. 423–425.

Primary Examiner—Donald T. Hajec
Attorney, Agent, or Firm—Scully, Scott, Murphy & Presser

[57] ABSTRACT

A method for separating diamonds from associated gangue in a diamondiferous material. The method comprises the steps of mixing the diamondiferous material with water to form a slurry and passing the slurry through laser radiation of known wavelength in the infra red part of the electromagnetic spectrum to cause Raman spectral scattering of the radiation from the slurry. The scattered radiation is collected and filtered to isolate diamond-relevant radiation and the filtered radiation is analyzed to determine whether it is indicative of the presence of diamond. Finally, on the basis of such analysis, high diamond content slurry is separated from low diamond content slurry.

20 Claims, 5 Drawing Sheets

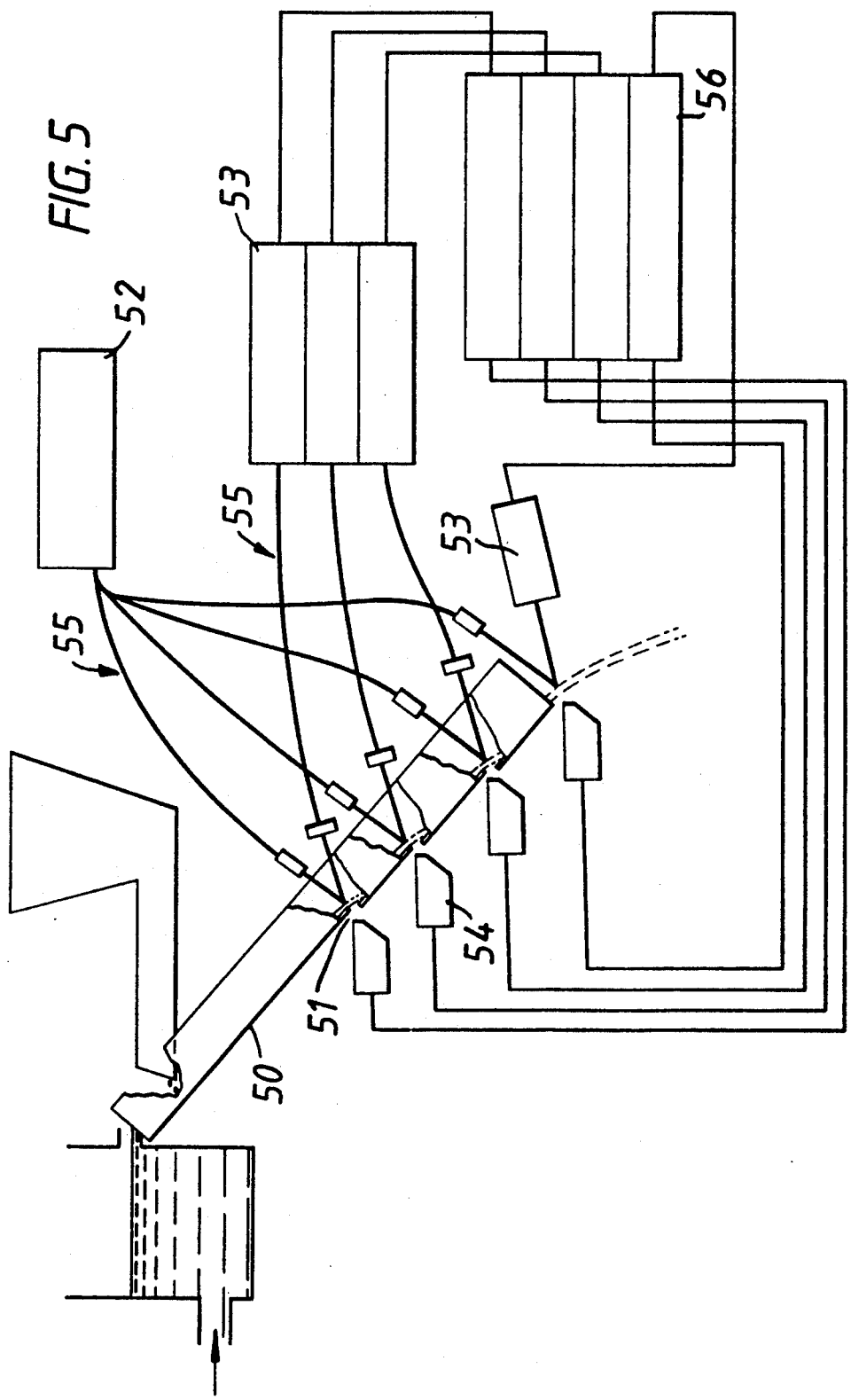

METHOD AND APPARATUS FOR SEPARATING DIAMONDS FROM ASSOCIATED GANGUE

BACKGROUND TO THE INVENTION

The present application is a continuation-in-part of U.S. patent application Ser. No. 488,378, filed Feb. 23, 1990, which was a continuation of Ser. No. 188,799, both now abandoned.

The present invention relates to the separation of diamonds from associated gangue.

Diamond bearing ores unlike most other ores have a very low ratio of diamond to associated waste material (known as gangue) and it can be as little as one to several million. Further, the diamond must be recovered undamaged from the ore and the presence of diamond in ores is not easily determined by chemical assay methods.

Diamonds occur in alluvial deposits or in kimberlite pipes. The ore is subjected to a series of mechanical enrichment processes involving sieving, crushing and density separation techniques to obtain a concentrate containing the diamonds, the tailings or gangue being discarded. The concentrate is then sized into a number of size ranges and passed through X-ray separators which detect the fluorescence of the diamonds (and a number of other materials) causing an air ejection system to displace the diamondiferous material from the non-diamondiferous material. The final selection of uncut diamonds is then made by hand.

UK patent application 2140555A relates to a method for the separation of diamonds from associated gangue comprising the steps of passing discrete units of diamondiferous ore through a beam of laser radiation capable of causing Raman spectral activation, detecting the scattered Raman radiation by means of a detector, the detector being adapted to actuate means for separating discrete units of diamond containing ore from the discrete units of non-diamond containing gangue, and collecting the separated discrete units. The application also discloses a separator suitable for use in separating diamonds comprising a source of laser radiation, means for passing discrete units of a diamond containing ore through the beam of laser radiation, detecting means for detecting scattered Raman radiation and means for separating discrete units of high diamond content from the flow of small diamond content gangue, the separating means being triggered by the detecting means.

In known methods of diamond separation, diamondiferous material for separation is transported by an endless conveyor belt, a continuous falling stream of material being discharged, from the end of the belt. The material is irradiated with X-rays or laser Raman radiation and a suitable detector is used to detect the ensuing fluorescence or reflected radiation, the output of the detector being arranged to control a device such as a compressed air nozzle to deflect the diamond containing material from the stream.

The diamondiferous material for separation is often moist or contains some water and a particular problem which arises is that the particles stick together or clog. They also stick to the conveyor belt. This can cause an irregular falling stream of material to occur from the end of the belt with consequent errors in the diamond separation process.

A further problem with a belt feed system if used in a sorting technique of the kind proposed in UK patent application 2140555A is the fact that the belt material itself may luminesce under the effects of incident laser radiation. This luminescence makes it more difficult to detect the Raman peak or band which is characteristic of diamond and which it is imperative to detect if the technique is to operate accurately.

In a belt feed system, the further problem that may exist is the fact that the conveyed particles may bump one another and generally move in random fashion, rendering it all the more difficult to separate the diamond particles from the associated gangue particles.

Furthermore, the UK patent application proposes the use of an argon ion laser operating at a characteristic wavelength of 514.5 nanometres. A problem associated with the use of a laser of this kind is the fact that fairly high levels of scattered background radiation can be generated, increasing the difficulty of detecting the Raman peak or band characteristic of diamond.

SUMMARY OF THE INVENTION

A first aspect of the present invention provides a method for separating diamonds from associated gangue in a diamondiferous material, the method comprising the steps of:

(a) mixing the diamondiferous material with a liquid wherein said liquid is water or a water containing solution to form a slurry;

(b) passing the slurry through laser radiation of known wavelength in the infra red part of the electromagnetic spectrum to cause Raman spectral scattering of the radiation from the slurry:

(c) collecting and filtering scattered radiation from the slurry, filtering being achieved by means of a filter system adapted to pass radiation in a narrow band including the Raman wavelength for diamond;

(d) detecting the filtered radiation with a detector;

(e) analyzing the filtered radiation to determine whether it is indicative of the presence of diamond; and (f) separating, on the basis of such analysis, high diamond content slurry from low diamond content slurry.

By the term "high diamond content slurry" is meant slurry having a higher proportion of diamonds from the diamondiferous material than the low diamond content slurry. Thus, the high diamond content slurry may contain all the diamonds from the diamondiferous material. Alternatively it may only contain a proportion of the diamonds, with a lower proportion being present in the low diamond content slurry. In the latter case, the low diamond content slurry may be subjected to further separation processes.

In the preferred form of the invention, the slurry is passed through laser radiation produced by a YAG or Nd-YAG laser.

Typically, the diamondiferous material is mixed with the liquid on an inclined chute so that the slurry moves under gravity down the chute. The slurry may be passed through the laser radiation, and the scattered radiation may be collected, while the slurry is moving down the chute. The preferred chute is made of metal, typically steel, and has a broad, flat-bottomed shape. To improve particle identification and location, it is also preferred that the speed of movement of the slurry down the chute is chosen for laminar flow conditions to prevail.

A second aspect of the invention provides an apparatus for separating diamonds from associated gangue in a diamondiferous material, the apparatus comprising:

(a) an inclined chute, (b) means for mixing the diamondiferous material with a liquid on the chute, said liquid being water or a water containing solution, to form a slurry that flows down the chute, the chute and mixing means being designed for the slurry to flow down the chute in laminar flow;

(c) a laser source for producing laser radiation at a known wavelength in the infra red part of the electromagnetic spectrum;

(d) means for taking the laser radiation to the slurry so that the radiation impinges on the slurry to cause Raman spectral scattering from the slurry;

(e) a filter system adapted to pass radiation in a narrow band including the Raman wavelength for diamond;

(f) means for collecting the scattered radiation and for taking it to the filter system;

(g) a radiation detector for detecting the filtered radiation;

(h) processor means for analyzing the filtered radiation to determine whether it is indicative of the presence of diamond; and (i) separating means actuable by the processor means to separate high diamond content slurry from low diamond content slurry.

A diode array detector may be used to detect the filtered radiation, the diode array detector effectively comprising a series of detectors in line. This enables a large portion of the spectrum to be examined simultaneously and using this detection technique, it is anticipated that the presence of diamonds can be determined in a time of the order of milliseconds or perhaps even faster. As an alternative, the detector may be an indium-gallium-arsenide detector.

The processor makes its determination of whether or not diamond is present by comparing the spectral data which it receives from the radiation detector with predetermined values of, say, the wavelength at which a spectral peak occurs, the peak size and the level of the peak above the background scatter.

It is also preferred to use arrays of optical fibres to take the radiation to the slurry and to collect the scattered radiation and take it to the filter system, since this makes it possible to position the laser source and analysis equipment remote from the diamondiferous material itself, thereby enhancing the security and convenience of the separation technique.

The diamondiferous material may be concentrated diamondiferous ore obtained by known concentration techniques. The diamondiferous ore may, for instance, be derived from mining or alluvial dredging operations.

It is envisaged that the invention may also be used for separating synthetic diamonds from associated material. It is intended that such associated material comes within the meaning of the term "gangue" in this specification.

BRIEF DESCRIPTION OF THE DRAWINGS

The invention will now be described by way of example only and with reference to the accompanying drawings in which:

FIG. 5 is a schematic view of apparatus of the invention using a chute with multiple ejector positions.

DESCRIPTION OF EMBODIMENTS

Figure 1:
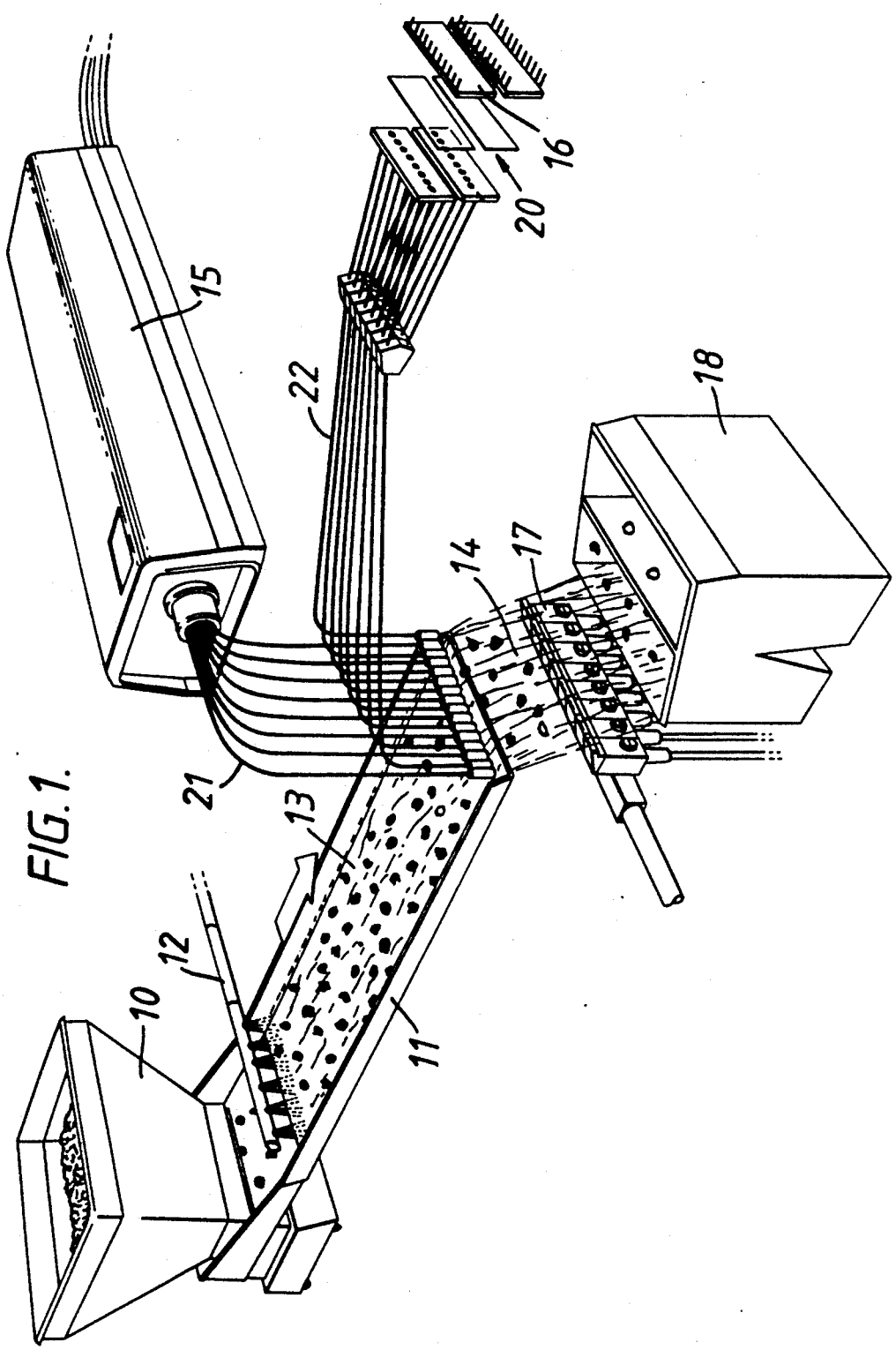
FIG. 1 is a diagrammatic perspective view of an apparatus of the invention.
Figure 2:
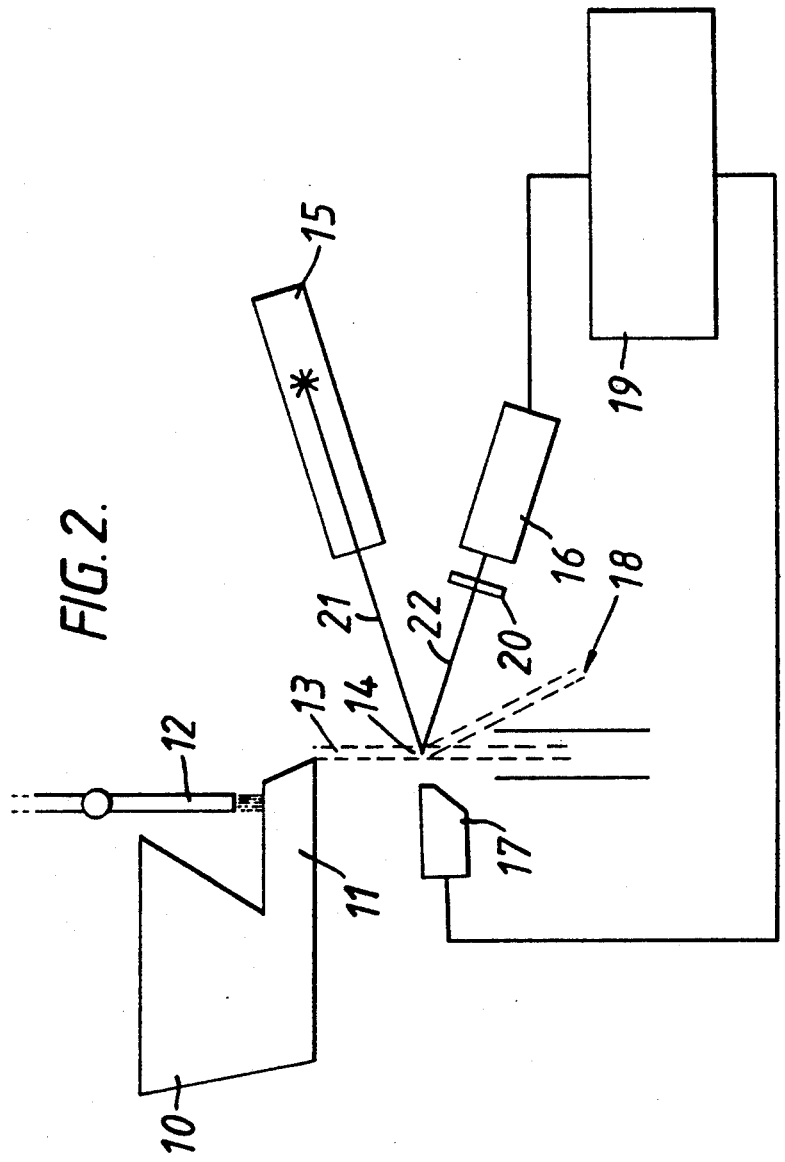
FIG. 2 is a schematic view of apparatus of the invention using a free fall technique.

In FIGS. 1 and 2, a vibratory feeder 10 is arranged to pass diamondiferous ore along a chute 11 of flat cross-section. A water supply 12 passes water into the ore to form a slurry 13 passing along the chute which eventually falls freely from the end of the chute.

A laser 15 is arranged to direct radiation into the falling slurry 14 so as to determine the presence of diamond. The laser radiation scattered by the Raman effect is filtered using filters 20 and is detected by a detector diode array 16. A compressed gas nozzle ejector 17 is located adjacent to and pointing at the falling slurry 14. An electronic microprocessor unit 19 linked to the detector is arranged to trigger the ejector so as to displace high diamond content slurry into an adjacent collector 18.

The preferred laser is a high power laser producing laser radiation in the infra red, and more particularly the near infra red, part of the electromagnetic spectrum. A YAG (yttrium-aluminum-garnet) laser or Nd-YAG (neodymium-YAG) laser, operating at a characteristic wavelength of 1064 nanometers is suitable. The laser is a continuous wave laser which may be air or water cooled and which produces up to 40 W of power.

The laser radiation is taken to the falling slurry by means of a system of optical fibres 21. The scattered Raman radiation is collected by a second optical fibre system 22 and is sent to the filter/detector. The filtering system may be a narrow band pass optical filter capable of passing radiation of + or −0.5 nanometre from the desired Raman wavelength, i.e. the wavelength at which the Raman peak or band for diamond occurs.

During use, the ore passing from the vibratory feeder 10 into the chute 11 is mixed with water to form a slurry 13. When the slurry reaches the end of the chute it falls freely downward from the end of the chute. Laser radiation from the source 15 impinges on the falling slurry 14 and the scattered Raman radiation is collected and detected by the detector diode array 16. If scattered Raman radiation due to the presence of diamond is detected by the detector, the detector sends a signal to an electronic microprocessor unit 19 which triggers the ejector 17 causing a puff of compressed gas to displace the high diamond content slurry into an adjacent collector 18. The remaining slurry passes downwards, unaffected by the ejector 17, to a further collector.

As stated previously, the filters 20 can consist of narrow band pass filters which pass a narrow band of radiation. In practice, this band will be centred on the characteristic wavelength for diamond, i.e. $1332^{cm-1}$. Extraneous radiation is filtered out. Since there may still be appreciable background radiation within the narrow pass band, it is possible for the filter system to pass further radiation in another narrow band slightly removed from the diamond band. Since the diamond peak is normally rather strong in comparison to the surrounding background radiation, there will be a marked difference in the readings obtained from the two bands, indicating with certainty that a diamond is present.

Figure 3:
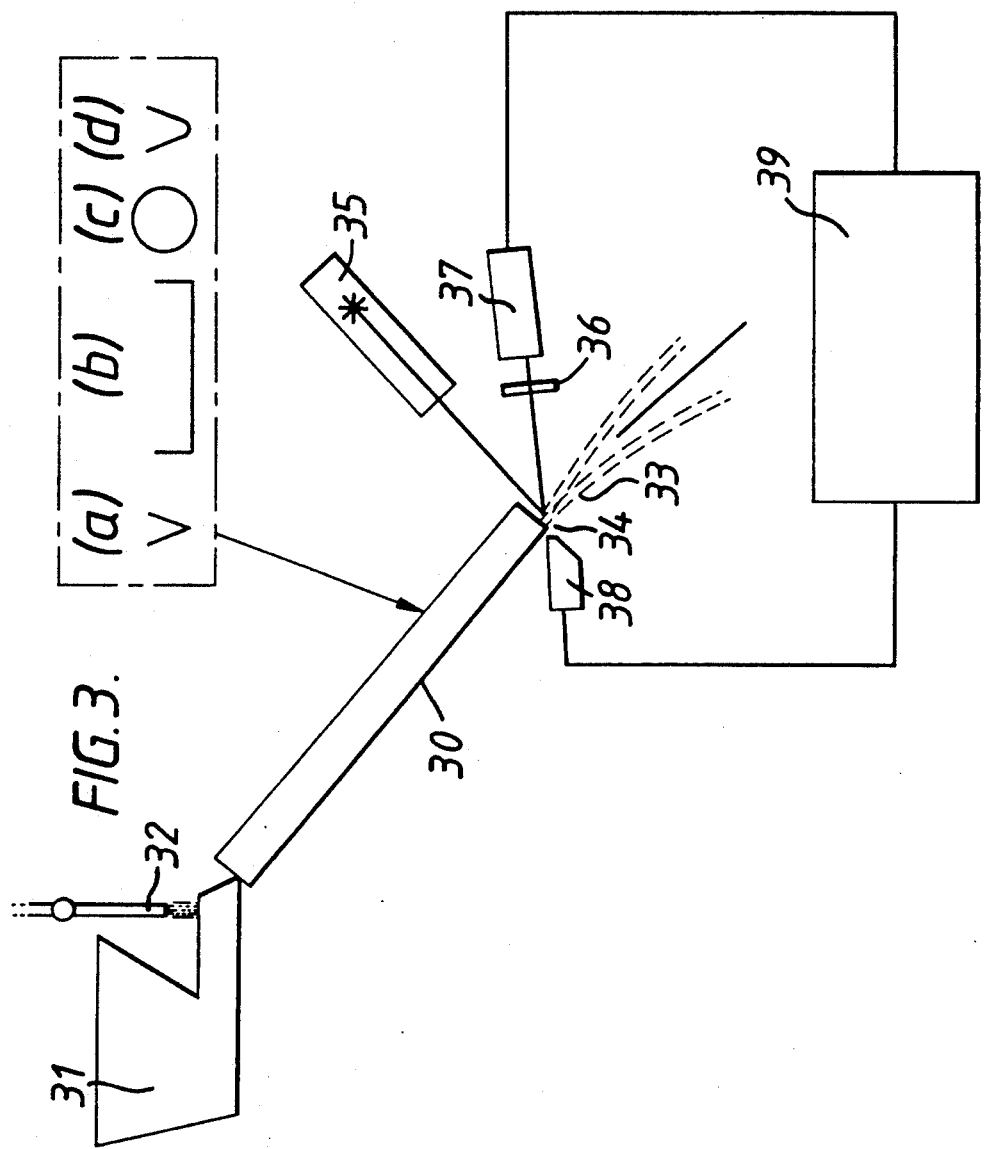
FIG. 3 is a schematic view of apparatus of the invention using a chute feed system, with various chute shapes illustrated at (a) to (d)

In FIG. 3, a vibratory feeder 31 is arranged to pass diamondiferous ore along a chute 30 inclined at about 60 to the horizontal. A water supply 32 passes water into the ore to form a slurry 33 passing along the chute which eventually falls freely downward from the end of the chute. A YAG or Nd-YAG laser 35 is arranged to direct radiation into the falling slurry 34 so as to determine the presence of diamond. The laser radiation scattered by the Raman effect is filtered using filters 36 and detected by a detector 37. A compressed gas nozzle ejector 38 is located adjacent to and pointing at the falling slurry 34. An electronic microprocessor unit 39 linked to the detector is arranged to trigger the ejector so as to displace high diamond content slurry into an adjacent collector. A number of alternative cross sections (a), (b), (c) and (d) for the chute are shown. The use of the inclined chute in combination with a water slurry enables the throughput of ore to be increased relative to a free fall arrangement.

Both embodiments described so far show the laser radiation impinging on the slurry while it is in free fall after having discharged from the end of the chute. In practice, it is also possible to irradiate the slurry, and collect the scattered radiation, while the slurry is actually on the chute. In many instances, this will in fact be preferred, particularly if the chute is flat-bottomed chute having the cross-section seen at (b) in FIG. 3.

The reason for this is that, on a flat chute, the particles are presented in a known plane, overcoming any focussing problems that may arise in collecting the scattered radiation.

Since the scattered radiation may be obscured or unduly attenuated in a slurry which is too turbid, it is preferred to operate the chute feed system in a laminar flow regime rather than a turbulent flow regime. Thus the inclination of the chute and other factors contributing to the speed of flow of the slurry on the chute will be chosen to result in a Reynolds number in the laminar flow regime.

Figure 4:
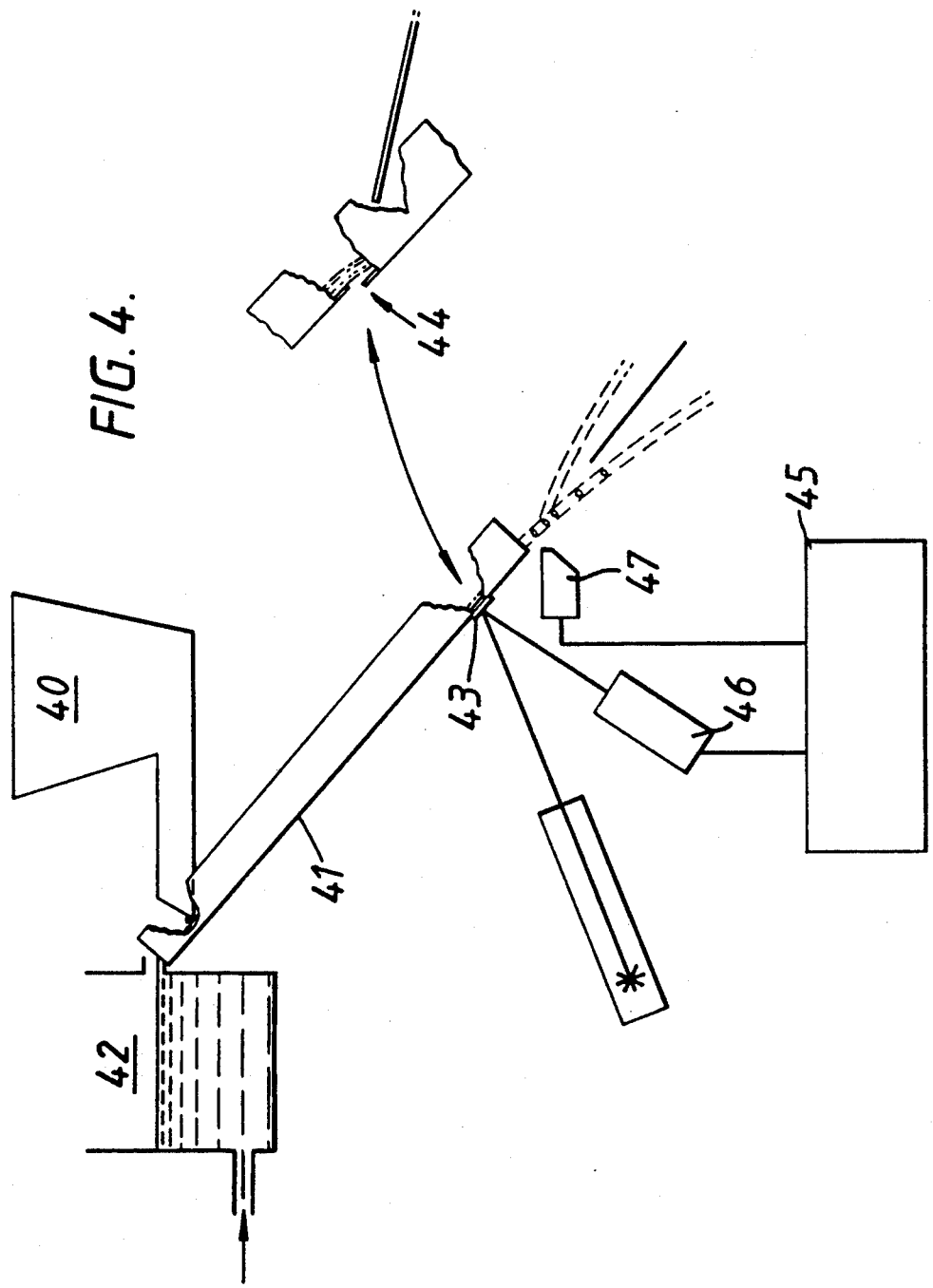
FIG. 4 is a schematic view of apparatus of the invention using a split chute system.

FIG. 4 shows an alternative arrangement in which the slurry is formed by feeding the ore from a vibratory feeder 40 into a V-shaped chute 41, the chute being supplied with water from an adjacent weir 42. Also the chute is equipped with a transparent window 43 (or a discontinuity 44 to form a cascade) so that laser radiation can be directed at the slurry and scattered Raman radiation detected from the slurry on the chute. A suitable electronic microprocessor 45 with delay capabilities is connected to the detector system 46 to enable accurate separation to be achieved by delaying the operation of the ejector 47 until the respective slurry is falling freely from the end of the chute.

It would of course be possible to use the FIG. 4 technique with a flat-bottomed chute.

FIG. 5 shows another alternative arrangement in which a plurality of separation stages can be made along a single chute 50. The chute is of broad cross section and has four cascades 51. Each cascade has a respective laser radiation supply 52, detector 53 and compressed air ejector 54. The laser, detector and ejector may be linked by an optical fibre network 55 and associated decision making electronics 56. This arrangement may be used with a high throughput of ore passing down a flat wide chute so that a coarse separation of diamonds can be obtained. Subsequently, a V-shaped chute may be used to achieve a fine separation of the diamonds.

The chutes used may be of various cross sections depending upon the throughput and the particle size of diamondiferous material. Thus, in general, a broad flat bottomed chute can be used for high throughput and coarse separation whereas a V-shaped chute can be used for low throughput and a fine separation.

As mentioned previously, a problem with conventional "dry" sorting methods is the fact that the material which is presented for sorting has some moisture content arising from the earlier processing steps carried out on it. The damp particles tend to stick or clog together, making it difficult to perform an accurate sort. It is of course conceivable that the particles could be thoroughly dried before presentation but this is not really a practical solution in view of the enormous cost that would be associated with drying equipment having the capacity to deal with the quantity of particulate material requiring sorting in, say, a mining or alluvial dredging operation. The present invention overcomes the sticking and clogging problem by presenting the particles in an aqueous slurry. Naturally, the addition of water enables the particles to disagglomerate and move apart from one another to increase the detectability and location of individual particles.

In addition to this, the slurry presentation system can lead to increased throughputs of material, since it is possible to move the particles in slurry form at a high rate on the chute. It is however desirable, as pointed out above, to maintain laminar flow conditions so that particle location is predictable.

A still further advantage of the slurry presentation of the particles is the fact that the aqueous content of the slurry serves a heat dissipation function. It will be appreciated that when a high power laser is used, some of the laser energy is converted to heat energy when the radiation strikes the target, in this case the slurry. The aqueous content of the slurry serves a continuous cooling function and prevents overheating of the apparatus in the vicinity. The heat dissipation advantage is enhanced if the chute is made of a metal such as steel, since localised heating of the chute will rapidly be conducted away and generally dissipated in the chute material. These features are particularly important when a high power YAG or Nd-Yag laser is used, since the use of such lasers increases the potential for localised heating of the apparatus.

It is believed that substantial advantages are to be gained by using a laser in the infra red part of the spectrum and particularly by using a YAG or Nd-YAG laser.

These advantages include the following:

a) the radiation produced by such lasers is eminently suitable for use with fibre optic radiation conveyance systems.

b) there is a fairly wide range of detectors that can be used to detect the scattered radiation. A particularly preferred detector is an indium-gallium-arsenide detector which can be used in place of the diode array detector described above.

c) most importantly, a YAG or Nd-YAG laser will not give rise to unduly high levels of background scatter which would make it difficult to detect the presence of a Raman peak characteristic of diamond.

It is also recognised that the use of a YAG or Nd-Yag laser has some disadvantages, notably its high power consumption when compared with, say, an argon ion laser. This disadvantage is however believed to more than off-set by the important advantages listed above which will, it is anticipated, lead to a substantial reduction in the further processing costs necessary to recover the diamonds.

Furthermore the infra red radiation produced by the laser is not in the visible part of the spectrum, increasing the danger of radiation injury to the operating personnel who will not be able to see the laser beam. This is not however considered to be a major defect, since the apparatus will in most cases be fully enclosed in a suitable housing both for safety and security.

I claim:

1. A method for separating diamonds from associated gangue in a diamondiferous material, comprising the steps of:
    a. mixing the diamondiferous material with a liquid comprising water or a water-containing solution to form a slurry;
    b. passing the slurry through laser radiation of known wavelength produced by a continuous wave YAG or Nd-YAG laser in the infrared part of the electromagnetic spectrum to cause Raman spectral scattering of radiation from the slurry;
    c. collecting and filtering radiation scattered from the slurry, with said filtering step passing radiation in a narrow band including the Raman wavelength for diamond;
    d. detecting the filtered radiation with a detector;
    e. analyzing the filtered radiation to determine whether it is indicative of the presence of diamond; and
    f. separating, on the basis of such analysis, high diamond content slurry from low diamond content slurry.

2. The method of claim 1, wherein said mixing step includes mixing the diamondiferous material with liquid on an inclined chute so that the slurry moves down the chute under gravity.

3. The method of claim 2, wherein said steps of passing the slurry through laser radiation and collecting scattered radiation are performed while the slurry is moving down the inclined chute.

4. The method of claim 3, wherein said mixing step includes mixing the diamondiferous material with liquid on an inclined metal chute.

5. The method of claim 3, wherein said mixing step includes mixing the diamondiferous material with liquid on an inclined broad, flat-bottomed chute.

6. The method of claim 3, wherein said mixing step includes mixing the diamondiferous material with liquid on an inclined chute wherein the chute is inclined at an angle such that the slurry flows down the chute with a laminar flow.

7. The method of claim 1, including the step of transferring laser radiation to the slurry by an optical fiber system.

8. The method of claim 7, wherein said collecting step includes collecting the scattered radiation and transferring the collected radiation to a filter system by an optical fiber system.

9. The method of claim 1, wherein said step of filtering scattered radiation includes passing scattered radiation having a wavelength of + or −0.5 nanometers from the Raman wavelength for diamond.

10. The method of claim 1, wherein said step of detecting includes detecting the filtered radiation with a diode array detector.

11. The method of claim 1, wherein said step of detecting includes detecting the filtered radiation with an indium-gallium-arsenide radiation detector.

12. An apparatus for separating diamonds from associated gangue in a diamondiferous material, comprising:
    a. an inclined chute;
    b. means for mixing the diamondiferous material with a liquid on the chute, said liquid being water or a water-containing solution, to form a slurry that flows down the chute, the chute and mixing means being designed for the slurry to flow down the chute in laminar flow;
    c. a continuous wave YAG or Nd-YAG laser source for producing laser radiation at a known wavelength in the infrared part of the electromagnetic spectrum;
    d. means for transferring the laser radiation to the slurry so that the radiation impinges on the slurry to cause Raman spectral scattering from the slurry;
    e. a filter system adapted to pass radiation in a narrow band including the Raman wavelength for diamond;
    f. means for collecting and transferring the scattered radiation to the filter system;
    g. a radiation detector for detecting the filtered radiation;
    h. processor means for analyzing the filtered radiation to determine whether it is indicative of the presence of diamond; and
    i. separating means actuable by the processor means to separate high diamond content slurry from low diamond content slurry.

13. The apparatus of claim 12, wherein said means for transferring the laser radiation to the slurry transfers the laser radiation to the slurry as it is flowing down the inclined chute.

14. The apparatus of claim 13, wherein the chute is a metal chute.

15. The apparatus of claim 13, wherein the chute is a broad, flat-bottomed chute.

16. The apparatus of claim 12, wherein said transferring means includes an optical fiber system.

17. The apparatus of claim 12, wherein said collecting and transferring means includes an optical fiber system.

18. The apparatus of claim 12, wherein said filter system passes radiation having a wavelength of + or −0.5 nanometers from the Raman wavelength for diamond.

19. The apparatus of claim 12, wherein said radiation detector comprises a diode array detector.

20. The apparatus of claim 12, wherein said radiation detector comprises an indium-gallium-arsenide radiation detector.

* * * * *